US008755885B2

(12) United States Patent
Deno et al.

(10) Patent No.: US 8,755,885 B2
(45) Date of Patent: Jun. 17, 2014

(54) SOFTWARE CONFIGURABLE MEDICAL DEVICE PLATFORM AND ASSOCIATED METHODS

(75) Inventors: D. Curtis Deno, Andover, MN (US); Jeffrey D. Wilkinson, Vadnais Heights, MN (US); John C. Stroebel, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 1669 days.

(21) Appl. No.: 11/116,569

(22) Filed: Apr. 28, 2005

(65) Prior Publication Data

US 2006/0079942 A1    Apr. 13, 2006

Related U.S. Application Data

(60) Provisional application No. 60/618,322, filed on Oct. 13, 2004.

(51) Int. Cl.
*A61N 1/362* (2006.01)

(52) U.S. Cl.
USPC ......... 607/27; 607/9; 607/30; 607/31; 607/59

(58) Field of Classification Search
USPC ................. 607/4, 5, 9, 15, 30–32, 59, 60, 27
See application file for complete search history.

(56) References Cited

U.S. PATENT DOCUMENTS

| 4,920,965 A | | 5/1990 | Funke et al. | |
|---|---|---|---|---|
| 5,048,521 A | * | 9/1991 | Pless et al. | 607/4 |
| 5,360,437 A | * | 11/1994 | Thompson | 607/30 |
| 5,421,830 A | * | 6/1995 | Epstein et al. | 607/30 |
| 5,456,691 A | * | 10/1995 | Snell | 607/30 |
| 5,725,559 A | * | 3/1998 | Alt et al. | 607/5 |
| 5,843,138 A | * | 12/1998 | Evers et al. | 607/30 |
| 6,216,036 B1 | * | 4/2001 | Jenkins et al. | 607/27 |
| 6,282,450 B1 | * | 8/2001 | Hartlaub et al. | 607/59 |

(Continued)

FOREIGN PATENT DOCUMENTS

| EP | 0532149 A1 | 4/1992 |
|---|---|---|
| EP | 0605970 A1 | 12/1993 |

OTHER PUBLICATIONS

Riley, R.E., et al. "Software Simulation of an Implantable Pacemaker." IEEE, 1983.*

(Continued)

*Primary Examiner* — Christopher D Koharski
*Assistant Examiner* — Pamela M Bays
(74) *Attorney, Agent, or Firm* — Reed A. Duthler; Stephen W. Bauer (57) ABSTRACT

The invention relates to medical devices such as pacemakers, pulse generators, cardioverter-defibrillators and the like and more particularly relates to modular and reconfigurable medical system platforms and methods of designing, testing, controlling and implementing diverse therapies, diagnostics, physiologic sensors and related instrumentation using said medical system platforms. Methods, systems and devices provide a new design platform for implantable and external medical devices such as pacemakers, defibrillators, neurostimulators, heart monitors, etc. A real-time, highly flexible system of software and hardware modules enables both prototypes and products to respond to patient and customer needs with greater design and manufacturing efficiency. Certain embodiments integrate a general-purpose processor with interface circuitry to provide a standard platform for implementing new and conventional therapies with software models rather than custom circuitry. The platform described may be used as a simulation environment, development and test platform and/or may be used as architecture for building new medical devices.

20 Claims, 5 Drawing Sheets

(56) References Cited

U.S. PATENT DOCUMENTS

| | | | |
|---|---|---|---|
| 6,438,408 B1 * | 8/2002 | Mulligan et al. | 600/510 |
| 6,584,356 B2 * | 6/2003 | Wassmund et al. | 607/30 |
| 6,754,533 B1 * | 6/2004 | Helfinstine et al. | 607/27 |
| 2003/0074029 A1 | 4/2003 | Deno et al. | |
| 2004/0167410 A1 | 8/2004 | Hettrick | |

OTHER PUBLICATIONS

Riley, R. E. et al, "Software Simulation of an Implantable Pacemaker." IEEE. 0195-4210/83/0000/0402$01.00. (1983): 402-405.*

* cited by examiner

SOFTWARE CONFIGURABLE MEDICAL DEVICE PLATFORM AND ASSOCIATED METHODS

CROSS-REFERENCE TO RELATED APPLICATION

This patent document hereby claims the benefit of the filing of prior provisional U.S. patent application Ser. No. 60/618,322 filed 13 Oct. 2004 and entitled, "Software Configurable Medical Device Platform and Associated Methods, by D. Curtis Deno et al.; the entire contents including all exhibits appended thereto are hereby incorporated herein by reference.

TECHNICAL FIELD

The invention relates to medical devices such as pacemakers, pulse generators, cardioverter-defibrillators and the like and more particularly relates to modular and reconfigurable medical system platforms and methods of designing, testing, controlling and implementing diverse therapies, diagnostics, physiologic sensors and related instrumentation using said medical system platforms.

BACKGROUND

Millions of lives worldwide have been saved or at least prolonged by various implanted and external medical devices such as pacemakers, defibrillators, electrocardiogram monitors and the like. As cardiac-related disorders such as congestive heart failure, ischemia, heart disease and the like become increasingly widespread, the percentage of the population having a need for an implantable, wearable or other medical device continues to rise.

The various types of medical devices presently available typically rely upon combinations of software, custom circuitry, sensors and actuators to detect, diagnose and treat a variety of cardiac events and disease states. Because of the high levels of reliability needed for these devices, the amount of effort required to design, test and implement most medical devices (and medical device components) is significant. In addition to being highly reliable, medical devices and components are typically designed to be extremely efficient in terms of space and electrical power consumption, for example, thereby further constraining designers of such devices. The need to keep medical devices small and power efficient is particularly significant in subcutaneous pacers and other devices that are implanted in a human body, since installation or repair may require the patient to undergo a surgical procedure.

Due to the stringent requirements of reliability, space efficiency and power consumption, most conventional medical devices presently contain large amounts of custom circuitry. While custom circuits are highly efficient, they can be particularly difficult to update and improve, since changes typically require physical modification or replacement of the actual circuits found in the device. As new therapies become available, frequently the only way for existing patients to gain access to the new therapy is to obtain an entirely new device. Further, simply testing new devices, components, therapy algorithms, diagnostic information or the like on custom circuitry can be cumbersome, since testing typically requires that custom circuits implementing the new technology be constructed.

Accordingly, it is desirable to create platforms, devices and/or techniques that are capable of easing the process of designing, testing and implementing new medical devices. Moreover, it is desirable to obtain a new development platform that can be readily modified to take advantage of new therapies. Furthermore, other desirable features and characteristics of the present invention will become apparent from the subsequent detailed description and the appended claims, taken in conjunction with the accompanying drawings and this background of the invention.

BRIEF DESCRIPTION

According to various embodiments, methods, a new design and/or implementation platform for implantable and external medical devices such as pacemakers, defibrillators, neurostimulators, heart monitors and the like is provided. A real-time and highly flexible system of software and hardware modules used for proof-of-concept prototype devices that can lead to commercial devices having features and capabilities responsive to clinician, patient and societal needs more rapidly and with greater design and manufacturing efficiency. An embodiment integrates a general purpose processor with interface circuitry to provide a standard platform for implementing new and conventional therapies with software models rather than custom circuitry. The platform described may be used as a simulation environment, as a development and test platform and/or may be used as a modular reconfigurable architecture for building new medical devices.

In certain embodiments, a platform for an implantable medical device configured to provide electrical stimulation or other therapy and to receive feedback data from the subject's body includes a controller and an interface. The controller includes a digital memory and a general-purpose digital processor operable to produce the electrical stimulation or other therapy as a function of the feedback data. The interface electrically couples any attached instrumentation (e.g., pacing leads, sensors, drug delivery devices, etc.) to the controller. The digital memory in the controller stores software instructions executable by the general-purpose digital processor to receive the feedback data from the interface and to process the feedback data using a modeling function to produce the electrical stimulation or other therapy. In a further embodiment, the computer-executable instructions are modifiable to adjust the modeling function without physically reconfiguring the controller or interface.

In other embodiments, the software instructions include various modules including an input module configured to receive the feedback data, a pacing engine configured to execute at least a portion of the modeling function and an output module configured to provide the electrical stimulation to the interface. Still further, various embodiments may include additional modules for simulating and/or providing various therapies such as neurostimulation, drug administration, and/or pacing therapies based upon myocardium recirculation fraction (RF), mechanical restitution (MR), ventricular synchrony, stroke volume, ejection fraction, physiologic parameters including subject activity, heart rate, myocardial refractoriness, temperature, posture, intra- and trans-thoracic fluid status (via impedance measurements), pacing capture threshold(s), arrhythmia episodes, heart rate variability, blood metrics (e.g., pressures, flows, and composition-oxygen content, calcium handling, pH, lactate levels and the like) and/or other factors.

Yet other embodiments include a medical device based upon a standard platform having a controller and an interface to a stimulus lead and a sensor lead. Aspects of these embodiments include a controller that executes software instructions to process feedback data using a modeling function to produce stimulus to the patient. The computer-executable instructions are modifiable to adjust the modeling function without physically reconfiguring the controller or interface.

In yet another embodiments, a software model for medical devices is provided. The software model is useful in testing new therapies, diagnostic information, circuitry and the like. Still other embodiments incorporate various techniques for designing, testing and implementing medical devices.

BRIEF DESCRIPTION OF DRAWINGS

Various embodiments will hereinafter be described in conjunction with the following drawing figures, wherein like numerals denote like elements, and.

DETAILED DESCRIPTION OF ILLUSTRATED EMBODIMENTS

The following detailed description is not intended to limit the invention or the application and uses of the invention, which has many different embodiments, features and advantages. Furthermore, there is no intention to be bound by any theory presented in the preceding background of the invention or the following detailed description of the drawings.

According to various embodiments, a new platform for creating medical device designs and implementations suitably incorporates modular hardware, flexible and modular software and real-time emulation and operation capabilities to produce rapid prototypes of new treatments, algorithms, devices and/or components. In a broad aspect, the new platform is based upon standard hardware and interfaces that can be readily modified through software changes to incorporate new treatments, alternate treatment parameters, new equipment or therapies or the like. Because the changes are made in software rather than hardware, the design and implementation of the medical device is greatly simplified. Moreover, because the new platform is based upon software constructs, it may be readily adapted for use in simulations, "hardware in the loop" tests of new devices or components, tests involving human or animal subjects and/or the like. Still further, the concepts and structures described herein may be used to formulate a new architecture for software-modifiable medical devices. Accordingly, the term "platform" as used herein is intended to be construed broadly as having application in modeling, design and/or implementation of medical devices and the like that may be used in conjunction with animal and/or human subjects.

Figure 1:
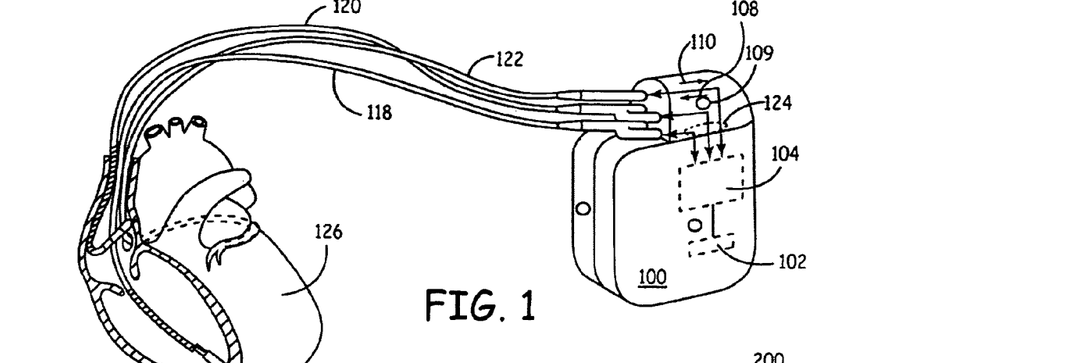
FIG. 1 is a diagram illustrating an medical device platform in association with a patient's heart.

Turning now to the drawings and with initial reference to FIG. 1, a medical device platform 100 suitably includes a controller 102 and an interface 104 to one or more types of instrumentation 124. Platform 100 emulates or implements a medical device such as a pacemaker, defibrillator, electrocardiogram monitor, blood pressure monitor, drug pump, insulin monitor, neurostimulator or the like. More particularly, platform 100 is shown in FIG. 1 as an implantable medical device (IMD) connected to monitor and/or apply one or more therapies to a patient's heart 126. In other embodiments, platform 100 is implemented as a test and/or design environment acting independently or in communication with a human or animal subject, as described more fully below.

As shown in FIG. 1, IMD implementations of platform 100 may be generally flat and thin to permit subcutaneous implantation within a human body, e.g., within upper thoracic regions or the lower abdominal region. IMD 100 may include a hermetically-sealed housing that encloses processor 102, interface 104 and other components as appropriate to produce the desired functionalities of the device. In various embodiments, platform 100 may be used to model and/or implement any IMD capable of measuring the heart rate or another parameter of a patient, including, but not limited to, a pacemaker, defibrillator, electrocardiogram monitor, blood pressure monitor, drug pump, insulin monitor, neurostimulator or the like. Such a device suitably collects and processes data 124 about heart 126 from one or more instrumentation sources (e.g. heart rate monitor, blood pressure monitor, PQRST waveform, etc.). Platform 100 may further provide therapy or other response to the patient as appropriate, and as described more fully below. An example of an IMD device is described in commonly-assigned U.S. Pat. No. 6,438,408B1, which issued to Mulligan et al. on Aug. 20, 2002.

Data 124 includes any signals transmitted or received between platform 100 and any attached instrumentation. As conceptualized herein, data 124 passing from platform 100 to heart 126 or another part of the subject's body is described as an outgoing signal 108, and data 124 received from heart 126 or another part of the subject's body is described as an incoming signal 110 (also referred to as a "feedback signal" or "feedback data"). The various signals 108 and 110 may be electrical signals applied on any lead or other type of instrumentation, or may be otherwise propagated in any manner. In practice, signals 108 and 110 may be implemented as voltage differences applied across multiple leads, as electrical currents applied on one or more leads, as digital and/or analog signals sent to any type of external instrumentation (e.g. drug delivery devices), and/or as any other type of signal.

The particular instrumentation coupled to platform 100 varies widely from embodiment to embodiment. In the example of FIG. 1, platform 100 is shown receiving a right ventricular endocardial lead 118, a left ventricular epicardial lead 122, and a right atrial endocardial lead 120. Other types of pacing instrumentation may include any type of unipolar and/or bipolar electrodes (e.g. any type of surface, endocardial, epicardial, cardiac-vein based and/or the like). In addition, the housing of IMD 100 may function as an electrode in various embodiments, either alone or along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event platform 100 is configured to provide pacing, cardioversion and/or defibrillation to heart 126. In addition, ventricular leads 118 and 122 may deliver pacing stimuli in a coordinated fashion to provide biventricular pacing, cardiac resynchronization or other benefits. Further, various electrode pairs (e.g. electrodes 118, 120, 122 in FIG. 1) may be used to sense cardiac events or conditions in any appropriate manner. Electrode pairs can be used for electrogram (EGM) and/or electrocardiogram (ECG) measurements, for example, that may be useful in diagnosing ischemia (e.g. from an elevated ST segment in a PQRST waveform) or other conditions, as well as in controlling pacing and other therapies. Impedance measurements between pairs of electrodes can be used to identify excessive amounts of fluid (e.g. pulmonary edema) in tissue located between the electrodes, and may also be used to detect inspiration and/or respiration based upon changes in fluid, which in turn can be used to resolve minute ventilation issues. Accordingly, the various leads 118,120 and 122 may be used individually and/or in concert with each other to obtain data 124 and/or to apply any number of therapies as appropriate.

Platform 100 may additionally or alternatively obtain input data 124 from other internal or external types of instrumentation (not shown) such as any type of mechanical sensor, metabolic sensor and/or the like. Various types mechanical sensors include pressure sensors (e.g., left/right ventricular or atrial chamber pressure, pulse pressure, aortic pressure estimated pulmonary arterial diastolic ("ePAD") pressure, plesmography/"cuff type" pressure sensors that wrap around vessels, etc.), flow sensors, accelerometers (e.g. for displacement, velocity and/or acceleration data), acoustic sensors (e.g. for detecting regurgitation sounds, sounds associated with cardiac cycle events (e.g. valve closures), etc.) and the like. Metabolic sensors used in various embodiments may include sensors for pH, lactate, oxygen, partial pressures of oxygen (PO2), saturated oxygen, saturated carbon dioxide, temperature, heart rate and/or the like. Again, various embodiments of platform 100 may be fashioned to interoperate with many different types of instrumentation or with various combinations of sensors, leads and/or other instrumentation.

In operation, controller 102 suitably analyzes data signals 108 received from the various instrumentation via interface 104, stores appropriate data in a memory or other storage device, and provides pacing and/or other therapy to the subject as appropriate. Suitable therapies used in various alternate embodiments may include application and/or modification of pacing, drug delivery, neurostimulation and/or other therapies. Alternatively or in addition to applying one or more therapies, an audible, visual or other alarm may be provided to notify the patient, a treating physician or any other party of any cardiac issues or episodes (e.g. arrhythmia, heart failure decompensation or other events). Alarms may be provided as these events occur so that that these conditions can be promptly treated. As will be described more fully below, the software-based nature of platform 100 allows for various sensed, computed and/or delivered parameters to be stored over time, thereby providing a powerful platform for design and testing of new devices and therapies, as well as providing enhanced capability for diagnosis, monitoring and treatment of the subject.

Figure 2:
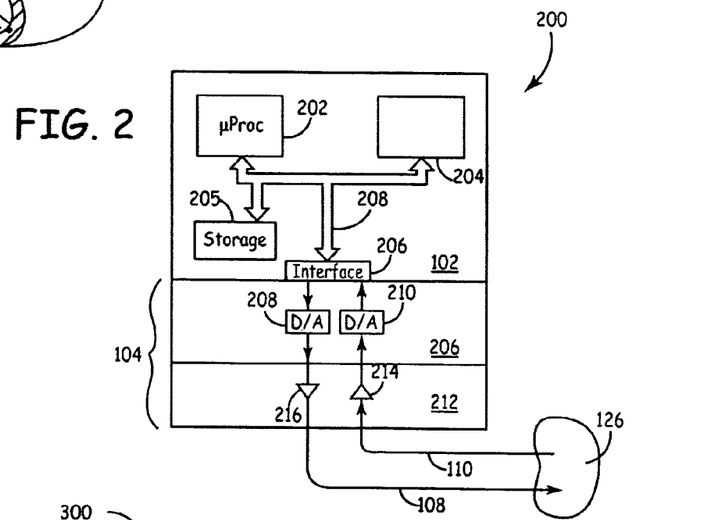
FIG. 2 is a conceptual block diagram showing an hardware system for a medical device.

FIG. 2 provides additional detail for a hardware system 200 suitable for use with platform 100 shown in FIG. 1. As described above, by designing a hardware environment based upon standard components, primary customization can be performed in software, thereby enabling a powerful platform for designing, testing and/or implementing new therapies and/or devices. Hardware system 200 may be implemented in any manner. With reference to FIG. 2, a hardware implementation 200 suitably includes a controller 102 in communication with an interface 104 having an input/output (I/O) module 206 and an analog module 212 for interfacing with the instrumentation coupled to platform 100 (see FIG. 1). In various embodiments, system 200 is implemented within the context of a conventional personal computer (PC), workstation or the like. Alternatively, system 200 may be implemented with any microcontroller or microprocessor-based card, device or system. In still other embodiments, controller 102, I/O portion 206 and/or analog interface 208 are formed on one or more common semi-conducting die that can be placed within a housing of a medical device for implantation into a patient.

Controller 102 is any system or component capable of controlling the various data processing functions of system 200. Controller 102 suitably includes a processor 202 that communicates with a digital memory 204 and an optional storage device 205 via a bus 208. In various embodiments, controller 102 is implemented with a conventional microcontroller or PC card, motherboard or the like. Such cards typically include one or more processors 202 such as a Pentium-class microprocessor available from the Intel Corporation of Santa Clara, Calif. or other sources. Alternatively, processor 202 may be implemented with any type of general or special purpose processor, microprocessor, digital signal processor, application specific integrated circuit (ASIC), field programmable gate array (FPGA) or other integrated or discrete logic circuitry programmed or otherwise configured to provide functionality as described herein.

Processor 202 executes instructions stored in digital memory 204 to provide functionality as described below. Instructions provided to processor 202 may be executed in any manner, using any data structures, architecture, programming language and/or other techniques. Memory 204 is any digital storage medium such as a static or dynamic random access memory, flash-type memory, or the like. Optional storage device 205 is any conventional device for storing digital data such as a hard drive, optical drive, writable CD-ROM or the like. Components 202, 204 and 205 inter-operate and communicate using any suitable bus 208 or other digital interconnection. In various embodiments, bus 208 is a peripheral component interface (PCI) bus or the like, although other bus architectures may be used in other embodiments. Bus 208 may also interlink a slot 207 or other interface to external devices and circuits such as interface 104, as described more fully below.

In embodiments that incorporate conductive leads or other instrumentation attached to platform 200, interface 104 suitably includes an input/output (I/O) module 206 that handles digital-to-analog (D/A) conversion between processor 202 and output signals 108 provided to attached instrumentation (see FIG. 1), as well as analog-to-digital (A/D) conversion from the analog input signals 110 received from the attached instrumentation. Converted digital equivalents to input signals 110 are appropriately provided to the various digital components of controller 102 for subsequent processing and/or storage. In various embodiments, (e.g. embodiments wherein platform 100 is intended solely as a testing or simulation environment) wherein no instrumentation is attached to platform 200, interface 104 may be disabled or omitted.

I/O module 206 may be implemented with any conventional or other circuitry, card or the like capable of providing an interface between controller 102 and analog interface 212. In various embodiments, I/O module 206 is a conventional D/A and/or D/A conversion card such as the Diamond MM-32 I/O cards available from the Diamond Systems Corp. of Newark, Calif., although other embodiments may use widely varying components.

Analog portion 212 of interface 104 suitably contains appropriate amplifier, filter and/or other circuitry 216, 214 for providing and receiving analog signals 108, 110 to/from any attached instrumentation. Analog module 212 may also provide for stimulation, amplification, sensor signal conditioning and other functions as appropriate. Analog circuitry 212 may be designed to interface platform 100 with the various types of instrumentation used in a particular embodiment, and will therefore vary widely from embodiment to embodiment. Various types of sensors or leads, for example, may have widely varying power and/or impedance parameters, thereby necessitating some variance in the interface circuitry between embodiments.

In operation, then, hardware 200 suitably obtains input signals 110 from the subject's body via leads, sensors and/or other instrumentation coupled to device 200. These analog signals 110 are received at analog portion 212, which provides any appropriate amplification 214 and provides the analog signal to I/O module 206. Module 206 converts the analog signal to a digital equivalent that can be provided to processor 202 via bus 208, as appropriate. Processor 202 suitably analyzes the data and/or stores the data in memory 204 as appropriate. In embodiments wherein platform 200 provides pacing and/or other therapy, processor 202 produces digital instructions that are provided to I/O module 206 via bus 208. The digital instructions are appropriately converted (by D/A 208) to analog signals 108 that can be amplified 216 and appropriately provided to pacing leads or other instrumentation as appropriate. In various embodiments, output signals 108 may be used to apply pacing, neurostimulation, drug and/or other therapies as appropriate.

As briefly mentioned above, hardware 200 may be constructed from conventional computing resources, with significantly reduced custom circuitry as compared to prior implantable devices. As a result, the functions, features and algorithms executed by hardware 200 may be readily and easily modified by simply modifying the software executed by processor 202. In various embodiments, particularly embodiments where controller 102 is implemented with conventional PC components, real-time modeling and the like can be provided using various conventional software environments such as Matlab, Simulink, Stateflow and/or the like, possibly in conjunction with custom code developed in any programming language such as the Visual Basic, .NET and/or Visual C/C++ programming environments available from the Microsoft Corp. of Redmond, Wash. Any alternate commercial and/or custom-built programming environments, languages, tools and applications could be used in a wide array of alternate embodiments, however.

Figure 3:
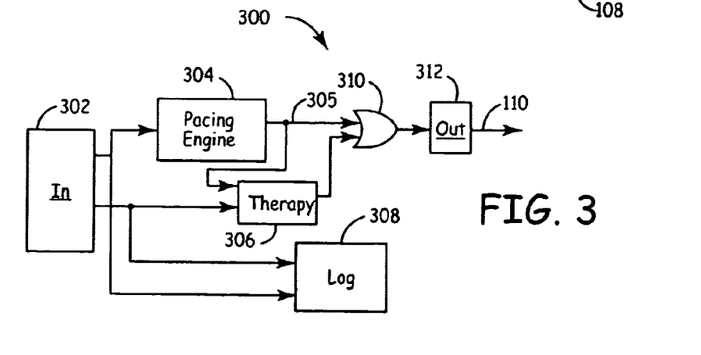
FIG. 3 is a block diagram of an software model for a medical device.

With reference now to FIG. 3, a software model 300 for modeling or implementing an implantable or external medical device suitably includes an input module 302, a pacing engine 304, a therapy processing module 306, a logging module 308 and an output module 312 as appropriate. Alternate embodiments may have widely varying modules depending upon the particular device or system being modeled or implemented. In a monitor that does not apply pacing or therapy, for example, pacing engine 304 and therapy module 306 may be omitted, along with output module 312. Similarly, other embodiments may provide additional therapies or functions, resulting in differently-organized or additional processing modules as appropriate. Each of the various modules shown in FIG. 3 may be implemented as software modules, objects, applications/applets or other constructs. In an one embodiment, each of the modules are implemented as Simulink/Stateflow objects, although other embodiments may implement the various modules with widely varying software environments or structures.

The various modules making up software model 300 suitably implement a modeling algorithm that processes input/feedback data to produce electrical stimulation or other therapy to the subject's heart 126 or body as appropriate. The algorithm may be modified by adjusting one or more software modules, or by otherwise modifying the software executing within model 300. Accordingly, the modeling algorithm can generally be adjusted using software controls, and without physically re-configuring controller 102 and/or interface 104. This functionality is useful in design and testing of therapies and devices. Moreover, the software constructs described herein may be used as an architecture for building software-configurable devices based upon standard hardware platforms. Accordingly, the software models described herein may have application across a wide array of design, testing and implementation environments.

Input module 302 suitably provides a source of data received from interface 104 (FIGS. 1 and 2), including feedback data 110 received from heart 126 (FIG. 1) or another part of the subject's body. Input module 302 may provide electrogram data, for example, as well as pressure data, oxygen sensor data, volume or blood flow data and/or the like. In various embodiments, input module 302 simply relays signals received from the various sensor amplifiers 214 found in analog interface 212 via A/D converters 210 in input/output module 210. Alternatively, input module generates the input signals and/or models the various sensor amplifiers 214 to adjust signal gains and/or connections as appropriate to obtain and route input signals as desired. Signal generation may be useful, for example, in simulations or in other aspects of designing or testing various devices, circuits or therapies prior to implementation in an IMD or other device.

Pacing module 304 is any software module, routine or collection of modules/routines capable of generating a pacing stimulus to heart 126 in response to signals received from input module 302. In various embodiments, pacing engine 304 contains modules to represent the various states of a conventional pacing device, including waiting for a cardiac event, pacing and refractory periods. Each of these states may be programmed as desired, with suitable timing periods, pacing pulse amplitudes and widths, and the like being configurable by adjusting the software parameters of the various modules, as described more fully below. Pacing module 304 suitably provides a pacing signal 305 to output module 312 that can be used to generate an atrial and/or ventricular pacing pulse at appropriate times.

Therapy module 306 suitably processes input data and/or pacing data to generate pacing or other therapeutic responses to heart 126 or another part of the patient's body as appropriate. The various therapies may be applied in conjunction with or in addition to pacing stimuli produced by pacing engine 304; accordingly, both therapy module 306 and pacing engine 304 can be conceptualized as providing a portion of the overall stimulation provided to the human or animal subject. The particular therapy applied by module 306 varies widely from embodiment to embodiment. Therapy module 306 may apply pacing therapies based, for example, upon myocardial recirculation fraction (RF), end systolic elastance, mechanical restitution (MR) and/or any other factors. Therapy module 306 may alternatively or additionally apply drug, neurostimulation or other therapies as appropriate, and as described more fully below. Further, many embodiments may simultaneously or alternately provide multiple therapies to the subject using one or more therapy modules 306.

Output module 312 suitably provides output signals 110 in an appropriate format for the instrumentation coupled to platform 100. Like input module 302, in various embodiments, output module 312 simply relays digital signals received from the processing modules (e.g. pacing engine 304 and/or therapy module 306) to pacing amplifiers 216 or other devices via D/A converters 210 in input/output module 210 (FIG. 2). Alternatively, output module 312 generates the analog signals and/or models the various pacing amplifiers 216 to adjust signal gains and/or connections as appropriate to obtain and route the pacing/output signals 108 as desired. In still other embodiments, output module 312 provides outputs to a computerized simulation or other model of a therapy or device, as described more fully below.

Logging module 308 suitably tracks and stores values of various signals propagating in software environment 300 over time. Various signals may be stored in memory 204 and/or storage device 205, and/or in any other appropriate location. This data may be subsequently retrieved by the patient or by an analyst, treating physician, clinic, researcher or other party to monitor the subject's cardiac events and other information as desired. Additional detail about the logging function is described below in conjunction with FIGS. 4 and 5.

In operation, software layout 300 suitably models the operation of an implantable or portable medical device such as a subcutaneous pacer or the like. Accordingly, input signals 110 representing feedback data from heart 126 or another organ are provided from sensor amplifiers 214 or another source (which may be simulated) to input module 302 as appropriate. This feedback data is processed according to a modeling algorithm by pacing engine 304 and/or therapy module 306 to compute appropriate responses 108 (e.g. pacing stimulation, etc.). In various embodiments, pacing engine 304 and/or therapy module 306 suitably provide signals to output module 312 to produce pacing events as desired. These signals may be combined (e.g. by optional OR operator 310) in any manner. Although only one pacing channel is shown in FIG. 3, many practical embodiments will include separate pacing channels for atrial and ventricular pacing or the like. Similarly, multiple therapy modules 306 may be provided for atrial or ventricular therapies, or to apply multiple therapies (e.g. pacing, neurostimulation and/or drug therapies) or the like in a wide array of alternate embodiments.

Figure 4:
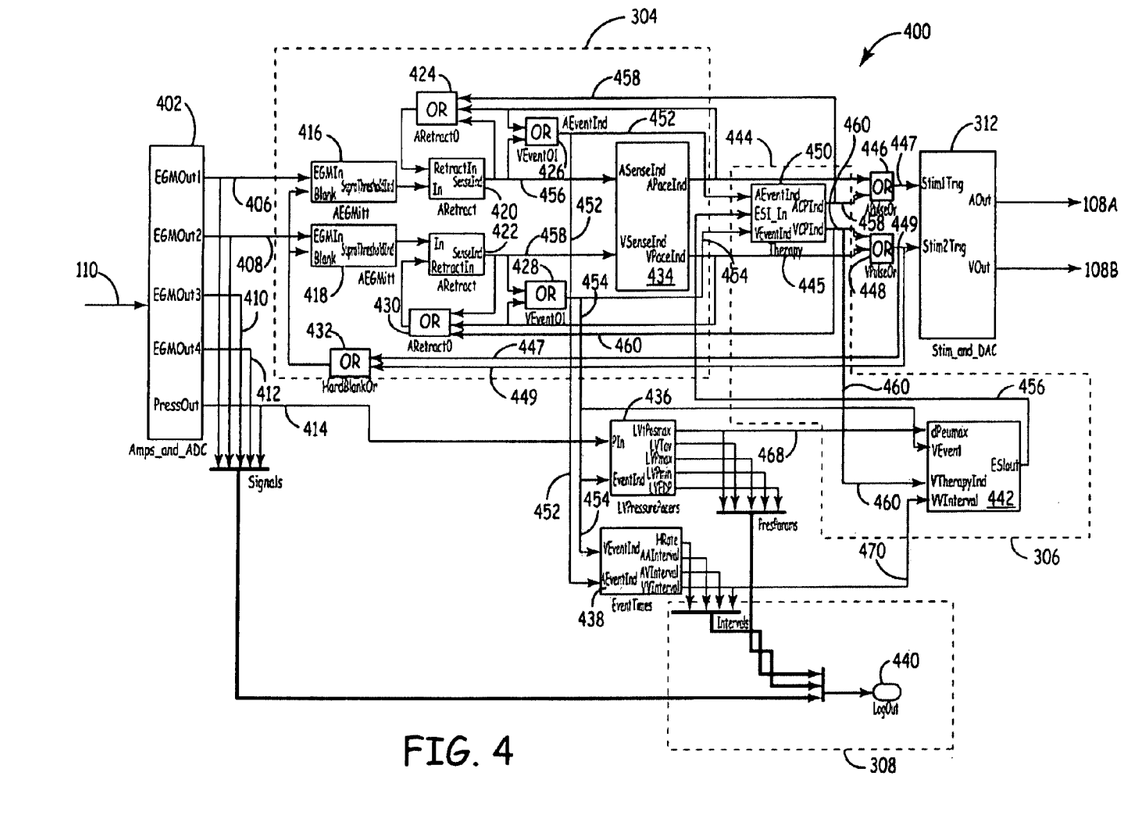
FIG. 4 is a block diagram showing additional detail of an software model for a medical device.

Additional detail of a software model 400 for a platform 100 (FIG. 1) is shown in FIG. 4. Like the more generalized implementation 300 described above, implementation 400 suitably includes an input module 402, a pacing engine 304, one or more therapy modules 306, an output module 312 and a logging module 308 as appropriate. The various functionalities described in software model 400 may be implemented with any combinations of modules, data structures, applications, or the like. Generally speaking, each module contains software instructions in an appropriate format to provide signal processing, data processing and/or other functionalities in any suitable manner. As discussed above and below, various alternate embodiments may include additional and/or alternate modules, depending upon the desired functionality of platform 100 and the particular instrumentation attached thereto. Further, model 400 may have application not only in actual IMDs and other devices, but also as a development and/or test environment for such devices.

Input module 402 suitably provides data signals that can be recorded and/or processed as appropriate by the various modules of model 400. In various embodiments, input module 402 receives feedback data 110 from interface 104 and processes this information as appropriate to provide useful input data to the various processing modules. Alternatively, input module 402 models the amplification and/or ADC functions of interface 104 to appropriately shape the various data signals provided as inputs to model 400. Furthermore, input module 402 may be configured in other embodiments to generate data that can be provided to a simulation, evaluation or other test running on model 400. Such functionality may be useful, for example, during design or evaluation of therapies, devices or the like. Accordingly, the various signals provided by input module 402 may be based upon real-time or other observed data, or may be generated electronically as appropriate for the various applications and embodiments.

The input module 402 of FIG. 4 is shown as providing various signals 406, 408, 410, 412 that are indicative of EGM data, as well as a signal 414 that is indicative of ventricular pressure. These signals may be based upon input signals 110 obtained from instrumentation attached to platform 100, and/or may be generated internally as appropriate. EGM signals 406, 408 are shown provided to separate paths of pacing engine 304 to control atrial and ventricular pacing, respectively, with EGM signals 410 and 412 provided to logging module 308. Similarly, ventricular pressure signal 414 is provided to a ventricular pressure computation module 436 that appropriately receives instantaneous data about ventricular pressure and computes various calculated values (e.g. dP/dt, maximum/minimum pressure, etc.). Alternate embodiments may provide additional and/or alternate signals to those shown in FIG. 4. Although FIG. 4 shows four EGM signals 406, 408, 410 and 412, for example, other embodiments may provide a single EGM signal to multiple modules, or may eliminate EGM functionality entirely. Similarly, input module 402 may or provide any number of data signals emanating from any type of sensors, cardiac leads and/or other instrumentation attached to platform 100, as appropriate.

Pacing engine 304 suitably includes appropriate modules and/or logic for applying atrial and/or ventricular pacing to a human or animal subject. Pacing is typically driven by electrical impulses 108 that are provided to heart 126 (FIG. 1) by way of electrodes attached to an IMD or other device. These impulses are generated by pacing engine 304 in response to feedback data 110 as appropriate. FIG. 4 shows one example of a pacing engine 304 that includes separate paths for atrial and ventricular pacing, as well as many discrete logic elements. As shown in FIG. 4, pacing engine 304 suitably includes an atrial and ventricular threshold indicators 416 and 418, atrial and ventricular refractory timers 420 and 422, pacing controller 434 and logic elements 424, 426, 428, 430 and 432. These various elements are shown for ease of understanding, but in practice may not appear in all embodiments. Indeed, the various functionalities and computations performed by pacing engine 304 may be differently organized or enhanced in any manner.

Generally speaking, pacing engine 304 monitors ECG information 406, 408 about the atria and ventricles of heart 126 to identify any naturally-occurring beats. Such beats are identified in atria or ventricles by threshold indicators 416 and 418, respectively. If an intrinsic (i.e. natural) beat is identified prior to a configurable timeout period by timers 420, 422, then timers 420, 422 reset the timeout period and wait for another beat. If a timeout occurs, then sensing logic (e.g. threshold detectors 416, 418) is temporarily disabled (i.e. "blanked") to prevent against false readings, and an electrical pace (signals 444, 445) is provided to the appropriate atrium or ventricle by pacing controller 434. After a suitable refractory time to allow the pacing current to dissipate, sensing logic 416, 418 is re-enabled to await another beat or timeout event. Atrial or ventricular events are identified when a natural depolarization (i.e. signals 456, 458) or paced depolarization (signals 444, 445) occur. FIG. 4 shows atrial and ventricular event indications as signals 452 and 454 emanating from OR operators 426 and 428, respectively.

Each of the various parameters commonly associated with pacing can be adjusted by modifying the software logic found in pacing engine 304. Threshold values in indicators 416, 418, for example, may be modified as appropriate to determine optimal settings or to customize the pacing for a particular subject. Similarly, timeout periods in timers 420, 422 can be modified, as can pacing magnitudes, widths, mode rates, etc. in pacing controller 434. Accordingly, pacing can be modeled or applied to a subject in a desired manner by simply adjusting software values within pacing module 304.

Signals 452, 454 may also be provided to logging module 308 to maintain a record 440 of such events. Similarly, various observed and/or computed values relating to the subject's status or health may be maintained in a log 440 for subsequent review by the patient, a treating physician, a clinic or another party. Information stored within log 440 varies, but may include any parameters or values of interest. In the example shown in FIG. 4, ECG data 410, 412 is maintained by logging module 308. Additionally, module 438 computes a number of values computed from signals 452, 454 including heart rate, AA pacing interval, AV pacing interval, VV pacing interval, etc. Similarly, module 436 computes several values derived from pressure data 414 obtained from a ventricular pressure sensor. Some or all of these computed values may be stored by logging module 308.

Data may be stored in log 440 in any manner. In various embodiments, data is stored at regular time intervals, with increased time resolution typically (although not necessarily) following an unknown event or event of interest (e.g. arrhythmia). Alternatively, data may be stored following events of interest, or according to any other scheme. Log 440 may be stored, for example, in memory 204 or storage device 205 (FIG. 2), although the particular location of stored data will vary from embodiment to embodiment.

In various further embodiments, logging module 308 optionally monitors one or more parameters stored in the log to identify events of interest, and provides an alarm or alert if such an event occurs. An alarm may be audible and/or visible, or may involve automatically contacting medical assistance or the like via an optional telemetry or telephony module within platform 100. Alarms may be configurable within software module 400 as appropriate.

Figure 5:
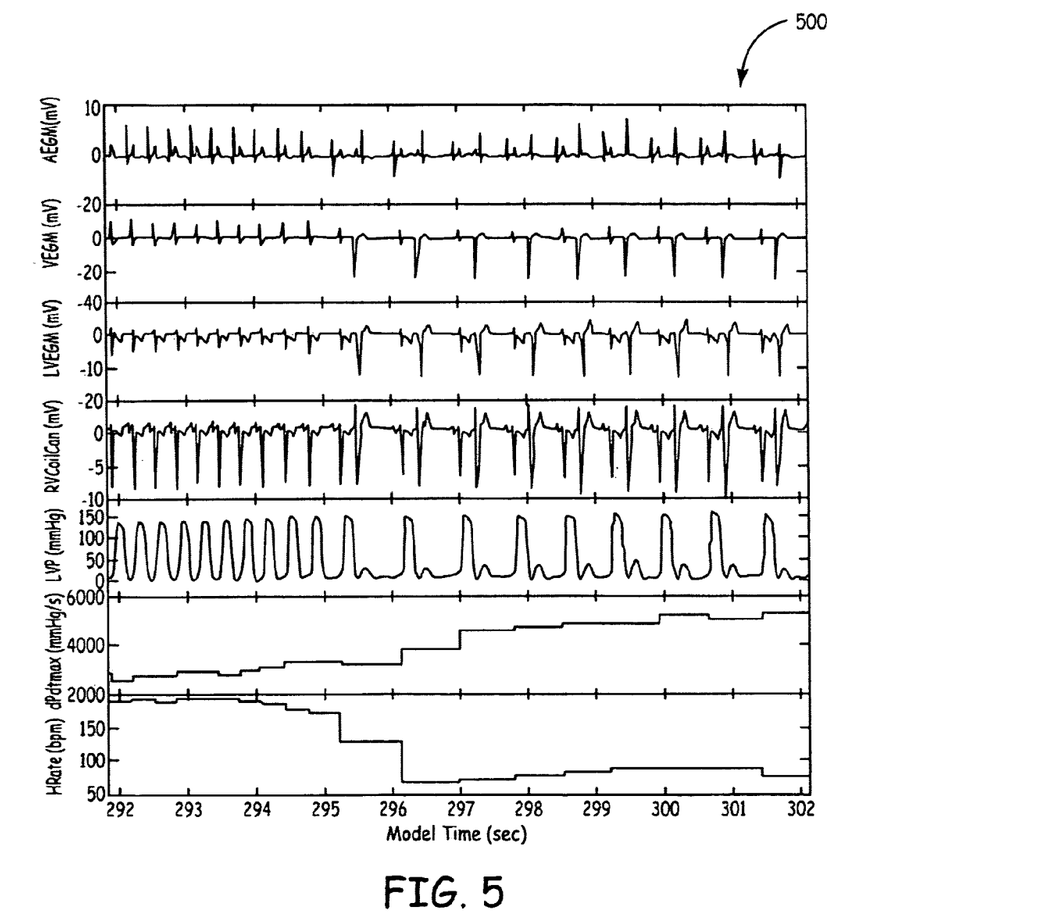
FIG. 5 is a series of graphs showing data values observed and/or modeled by a software model.

Data stored within logging module 308 may be retrieved and processed as appropriate. In embodiments wherein model 400 is embedded within an IMD or other production device, data may be obtained via telemetry or other techniques and plotted or otherwise manipulated as appropriate. In various embodiments (particularly those used in laboratory settings), software model 400 is able to present the data graphically or otherwise. Examples of various signals observed during a sample real-time simulation are shown in FIG. 5. FIG. 5 is intended merely to show the capabilities of one embodiment of a simulation/modeling environment, however, and other embodiments may track additional signals, fewer signals, alternate signals and/or no signals at all, as appropriate.

With reference again to FIG. 4, model 400 may be optionally configured to apply one or more therapies to the subject in place of or in addition to conventional pacing. In the embodiment of FIG. 4, therapy module 306 includes a controller module 442 that provides derived extrasystolic interval (ESI) data 456 to a therapy pacing module 450. The ESI data is processed at module 450 to adjust the pacing in a human or animal subject to allow for tracking of calcium reuptake, as described more fully below. Each of the therapy modules 442, 450 may be configured using software abstractions that can be readily modified to adjust or tune the therapy applied. Examples of therapies that could be incorporated in various embodiments, include, without limitation, pacing therapy (e.g. cardiac resynchronization therapy (CRT), paired/coupled pacing, bradycardia pacing, tachycardia pacing), anti-tachycardia pacing (ATP), cardioversion therapy, defibrillation therapy, and the like. Moreover, various non-pacing theories (e.g. pharmaceutical application, neurostimulation, etc.) could be alternatively or additionally applied using any type of instrumentation as appropriate.

Pacing signals 444, 445 produced by pacing engine 304 and any pacing signals (e.g. signals 458, 460) produced by any therapy modules 450 present in software model 400 may be provided to output module 312, which suitably converts the received signals to output signals 108A-B that can be provided to interface 104 (FIGS. 1-2) or otherwise processed as appropriate. In various embodiments (particularly those used in laboratory settings), output module 312 does not provide actual output signals 108A-B, but rather emulates some or all of the functionalities of interface 104 and/or attached instrumentation to facilitate operation as a simulation or other test platform. In the embodiment shown in FIG. 4, atrial and ventricular pacing signals are combined by logic operators 446, 448 to create combined signals 447, 449 that are provided to output module 312, although other embodiments may process the various signals in a different manner.

In operation, then, model 400 suitably provides pacing and/or other outputs 108 in response to feedback data 110 obtained from interface 104 (FIG. 1). Although the following section describes one embodiment that is concerned with recirculation fraction of the myocardium, the concepts set forth herein could be applied to any number of therapies and alternate embodiments. The particular therapies that can be applied by software model 400 are therefore very diverse, and differ dramatically from embodiment to embodiment.

The software model 400 shown in FIG. 4 is configured to monitor calcium reuptake in a patient. Because alterations in intracellular handling of calcium ($Ca^{+2}$) are known to be associated with congestive heart failure (CHF), changes in intracellular calcium regulation can be directly correlated to the contractile status of a patient's heart, and may be indicative of the onset and/or progression of CHF and other conditions. One technique for evaluating calcium regulation involves monitoring the force-interval property of the myocardium using the contractile parameter $dP/dt_{max}$ 468, which is in computed in model 400 by processing module 436 based upon feedback data 108, 414 obtained from a ventricular pressure monitor. More particularly, augmentation in dP/dt observed following a cardiac perturbation (e.g. an extra-systole, pre-mature ventricular contraction (PVC), or the like) can be quantified and tracked over time (e.g. by logging module 308) to identify changes in intracellular calcium regulation. Factors that may be monitored include the degree of systolic augmentation, as well as the time to recover from augmentation, and the like. Accordingly, the amount of augmentation following a heart beat perturbation can be a good indicator of the intracellular calcium regulation, and may provide insight into the overall hemodynamic status of the patient. In particular, measuring augmentation following a heart rate perturbation is believed to be useful in identifying patients at risk for CHF decompensation or sudden cardiac death.

To implement a treatment based upon recirculation fraction (RF) of the myocardium, then, system 400 applies a premature ventricular contraction (PVC) or other cardiac disturbance to the subject and then monitors the rate of decay of post-extrasystolic augmentation (PESP) over a series of heart cycles. A cardiac disturbance may be produced by simply providing an appropriate pacing signal 458, 460 from module 450 at an appropriate time during the subject's cardiac cycle. By monitoring $dP/dt_{max}$ during the time following the disturbance, a value for recirculation fraction can be computed. One technique for processing RF data involves monitoring the rate of change in $dP/dt_{max}$, which corresponds to the second time derivative of the ventricular pressure. This computation may take place within model 400, and/or may take place outside of the model based upon information maintained within logging module 308.

RF data obtained by system 400 could be used for enhanced monitoring, diagnosis and/or therapeutic functions as appropriate. System 400 may store diagnostic data in log 440, for example, or may activate an alarm to the patient if immediate medical attention is required, or may take other action as appropriate. In further embodiments, system 400 administers or adjusts an appropriate therapy or other response when such treatment or adjustment to the treatment is warranted. In a further embodiment, augmentation may be used to determine optimal settings for a pacing device, or for optimal delivery of a pharmaceutical or other therapy. In practice, post-turbulent augmentation can be effectively manipulated and monitored by mechanisms present in many conventional medical devices, thus making augmentation a very effective parameter for monitoring or improving a patient's cardiac health. Additional data about augmentation and recirculation fraction may be found in U.S. Pat. No. 6,438,408 and in US Patent Publication No. US 2003/0074029A1.

The various concepts and structures set forth above can be implemented in various settings and environments, including design/prototyping, testing and implementation of devices for use with humans, animals (e.g. canines, swine) and/or other subjects. With reference again to FIG. 2, for example, platform 200 may be used as a development and/or prototyping platform that is based upon conventional components. That is, controller 102 may be implemented with a conventional personal computer with an attached I/O module 206 that interoperates with analog circuitry 212 and any attached instrumentation as appropriate. Such a platform can be readily configured with simulation software (e.g. Simulink, Labview or the like) that can be programmed to execute a software model 300, 400 that can in turn be used to direct or design the performance of an implantable or other device. Similarly, the hardware architecture shown in FIG. 2 may be compressed into a chip or other platform 100 suitable for use in an implantable, wearable or other device. In such embodiments, a controller 102 executes a software model 300, 400 to implement medical device functionalities as appropriate, with data communications to and from attached instrumentation being handled through interface 104. In still other embodiments, software models 300, 400 may be used on conventional computing hardware in the absence of interface 104 to provide a real-time (or faster than real-time) software simulation of a medical device.

Figure 6:
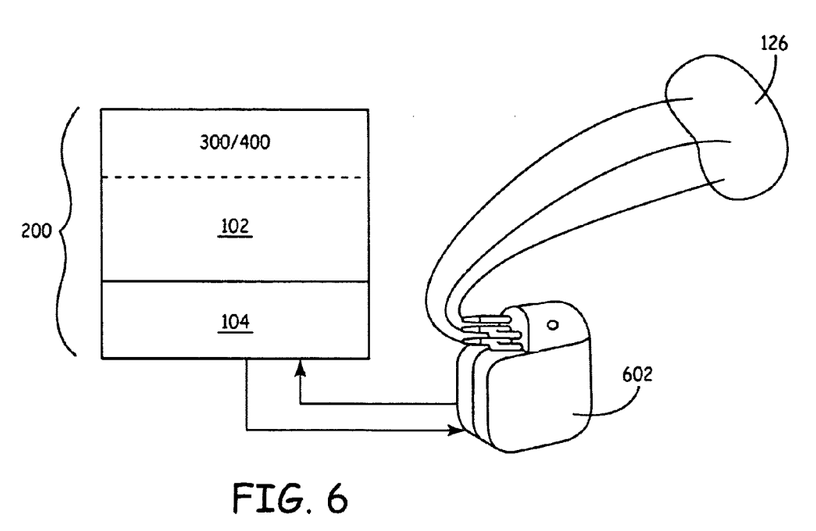
FIG. 6 is a schematic drawing, partially in perspective, of a reconfigurable cardiac apparatus according to one embodiment of the invention.
Figure 7:
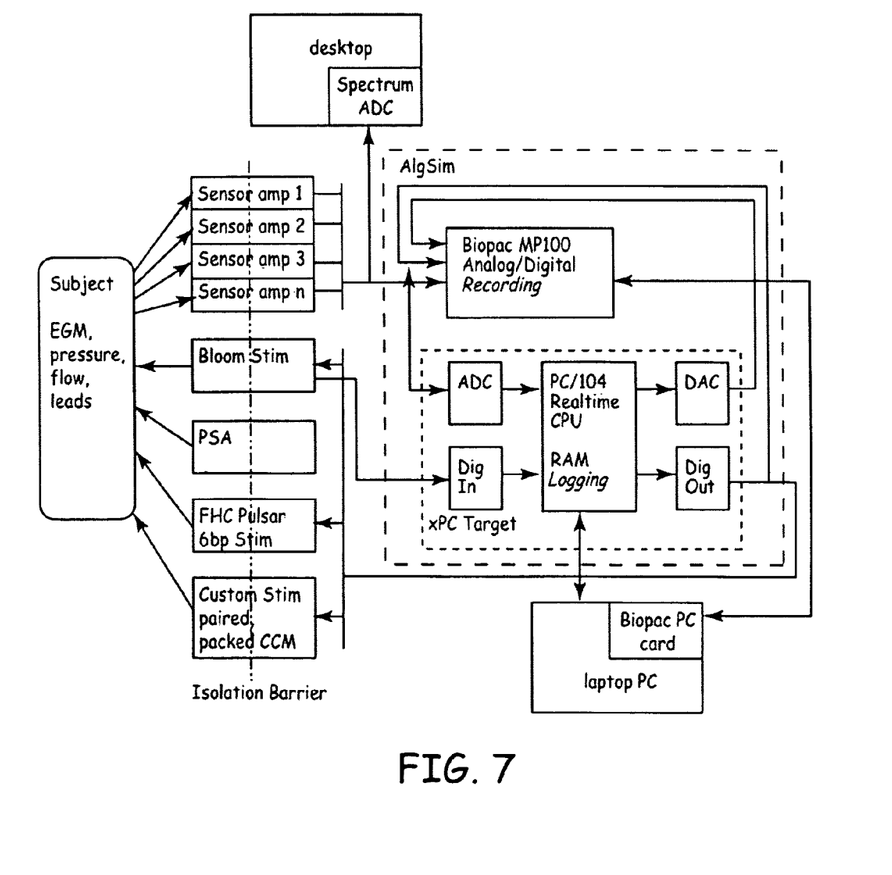
FIG. 7 depicts a schematic of an embodiment of the invention wherein a pair of discrete computers (e.g., desktop and laptop) are coupled to a reconfigurable cardiac apparatus according to the invention.

In other embodiments, and with reference now to FIG. 6, the hardware and/or software structures described herein may be used to test, evaluate or design an external hardware component 602. In such "hardware in the loop" embodiments, platform 200 suitably intercommunicates with an external component 602 for data processing or the like. If component 602 is a sensor, for example, platform 200 may provide a pacing engine, data logging and/or other functionality used to test the sensor without requiring a separate pacemaker or other device. Other types of hardware (including sensors, electrodes, other types of instrumentation. Further, the software model 300/400 executed by platform 200 can be modified as appropriate to test various parameters, features or other aspects of hardware 602, thereby allowing for improved design and implementation.

Accordingly, various methods, systems and devices for designing, testing and implementing various medical devices are provided. The platform uses software to model the various functionalities of the device, thereby eliminating much of the custom hardware previously required to implement such devices. Furthermore, by providing a software development environment, new therapies and devices may be rapidly tested and implemented, thereby speeding time to market and reducing the costs of design and implementation.

While certain embodiments have been presented in the foregoing detailed description, it should be appreciated that a vast number of variations exist. It should also be appreciated that these certain embodiments are only examples, and are not intended to limit the scope, applicability, or configuration of the invention in any way. Rather, the foregoing detailed description will provide a convenient road map for implementing an embodiment of the invention. Various changes may be made in the function and arrangement of elements described in an embodiment without departing from the scope of the invention as set forth in the appended claims and their legal equivalents.

The invention claimed is:

1. A platform adapted to provide electrical stimulation to a patient's heart and to receive data from physiologic instrumentation coupled to the patient, said platform comprising:
   a controller comprising a digital processor and a digital memory, wherein the controller operatively provides electrical stimulation therapy to the patient's heart responsive to the data from the physiologic instrumentation; and
   an interface electrically coupling the controller to the physiologic instrumentation; and
   wherein the digital memory comprises software instructions executable by the digital processor to receive the data via the interface and to process the data using a modeling algorithm which simulates operations of analog amplifier circuitry to control delivery of the electrical stimulation.

2. A platform according to claim 1 wherein the digital memory comprises software instructions executable by the digital processor to receive the data via the interface and to process the data using a modeling algorithm which simulates operations of analog pacing amplifier circuitry to control delivery of the electrical stimulation.

3. A platform according to claim 2, wherein the software instructions are modifiable to adjust at least one parameter of the electrical stimulation without physically reconfiguring the controller or interface.

4. A platform according to claim 3, wherein the software instructions comprise an input module configured to receive the data, a pacing engine module configured to deliver the electrical stimulation therapy and an output module configured to provide information regarding at least one of an operating parameter of the first electrical stimulation therapy and the physiologic instrumentation to the interface.

5. A platform according to claim 4, wherein the pacing engine comprises instructions defining an atrial therapy and a ventricular therapy for delivery to atria and ventricles of the patient's heart, respectively.

6. A platform according to claim 1 wherein the digital memory comprises software instructions executable by the digital processor to receive the data via the interface and to process the data using a modeling algorithm which simulates operations of analog sensor amplifier circuitry to control data from the physiologic instrumentation.

7. A platform according to claim 6, wherein the software instructions are modifiable to adjust at least one aspect of the data from the physiologic instrumentation without physically reconfiguring the controller or interface.

8. A platform according to claim 7, wherein the software instructions comprise an input module configured to receive the data, a pacing engine module configured to deliver a first electrical stimulation therapy and an output module configured to provide information regarding at least one of an operating parameter of the first electrical stimulation therapy and the physiologic instrumentation to the interface.

9. A platform according to claim 8, wherein the pacing engine comprises instructions defining an atrial therapy and a ventricular therapy for delivery to atria and ventricles of the patient's heart, respectively.

10. An apparatus for providing electrical stimulation to a patient's heart responsive to physiologic instrumentation coupled to the patient; comprising:
  a controller comprising a digital processor and a digital memory, the controller comprising means for providing an electrical stimulation therapy to the patient's heart responsive to the data from the physiologic instrumentation; and
  an interface electrically coupling the controller to the physiologic instrumentation; and
  wherein the digital memory comprises software instructions executable by the digital processor to process the data received via the interface using a modeling algorithm which simulates operations of analog amplifier circuitry.

11. An apparatus platform according to claim 10 wherein the digital memory comprises software instructions executable by the digital processor to receive the data via the interface and to process the data using a modeling algorithm which simulates operations of analog pacing amplifier circuitry to control delivery of the electrical stimulation.

12. An apparatus according to claim 11, wherein the software instructions are modifiable to adjust at least one parameter of the electrical stimulation without physically reconfiguring the controller or interface.

13. An apparatus according to claim 11, wherein the software instructions comprise an input module configured to receive the data, a pacing engine module configured to deliver a first electrical stimulation therapy and an output module configured to provide information regarding at least one of an operating parameter of the first electrical stimulation therapy and the physiologic instrumentation to the interface.

14. An apparatus according to claim 13, wherein the pacing engine comprises instructions defining an atrial therapy and a ventricular therapy for delivery to atria and ventricles of the patient's heart, respectively.

15. An apparatus according to claim 11 wherein the digital memory comprises software instructions executable by the digital processor to receive the data via the interface and to process the data using a modeling algorithm which simulates operations of analog sensor amplifier circuitry to control data from the physiologic instrumentation.

16. An apparatus according to claim 15, wherein the software instructions are modifiable to adjust at least one aspect of the data from the physiologic instrumentation without physically reconfiguring the controller or interface.

17. An apparatus according to claim 16, wherein the software instructions comprise an input module configured to receive the data, a pacing engine module configured to deliver a first electrical stimulation therapy and an output module configured to provide information regarding at least one of an operating parameter of the first electrical stimulation therapy and the physiologic instrumentation to the interface.

18. An apparatus according to claim 17, wherein the pacing engine comprises instructions defining an atrial therapy and a ventricular therapy for delivery to atria and ventricles of the patient's heart, respectively.

19. An apparatus for providing electrical stimulation to a patient's heart responsive to physiologic instrumentation coupled to the patient; comprising:
  means for providing an electrical stimulation therapy to the patient's heart responsive to the data from the physiologic instrumentation, comprising a digital processor and a digital memory; and
  an interface electrically coupling the controller to the physiologic instrumentation; and
  wherein the digital memory comprises software instructions executable by the general-purpose digital processor to process the data received via the interface using a modeling algorithm which simulates operations of analog amplifier circuitry.

20. An apparatus according to claim 19 wherein the physiologic instrumentation comprises a cardiac electrode lead.

* * * * *